United States Patent [19]

Silvern

[11] Patent Number: 4,490,142
[45] Date of Patent: Dec. 25, 1984

[54] CARPULE SYRINGE WITH RAPIDLY ACTING MECHANISM FOR CONTROLLABLY POSITIVELY RETAINING THE HUB OF A HYPODERMIC NEEDLE

[76] Inventor: Rubin D. Silvern, 12 Sulgrave Rd., Scarsdale, N.Y. 10583

[21] Appl. No.: 525,119

[22] Filed: Aug. 22, 1983

Related U.S. Application Data

[63] Continuation-in-part of Ser. No. 360,605, May 21, 1982, abandoned.

[51] Int. Cl.³ .............................................. A61M 5/00
[52] U.S. Cl. ................................................... 604/241
[58] Field of Search ............................... 604/239–243, 604/263, 187, 206, 218

[56] References Cited

U.S. PATENT DOCUMENTS 1,591,761  7/1926  Haines ................................. 604/242
2,047,512  7/1936  Kauffman .......................... 604/240
2,604,890  7/1952  Burnside ............................ 604/241
2,695,613  11/1954 MacGregor ....................... 604/239
2,806,473  9/1957  Lingley ............................. 604/243

Primary Examiner—John D. Yasko
Attorney, Agent, or Firm—Kirschstein, Kirschstein, Ottinger & Israel

[57] ABSTRACT

A carpule syringe including a frame that receives a carpule the front end of which is closed by a thin elastomeric membrane which is pierced by a short rearwardly extending pointed end of a double ended hypodermic needle extending from the hub. The pointed front end of the needle is designed for injection into a patient. The hub of the needle has a rearwardly tapering socket for frictional engagement on a forwardly tapered tubular extension of a tubular plug that is secured into a threaded female bore at the delivery end of the carpule frame. To prevent accidental displacement of the needle hub, the same is detachably engaged by a pair of clamping arms that are pivotally mounted on a ring located at the front end of the syringe frame and are biased toward closed position.

6 Claims, 6 Drawing Figures

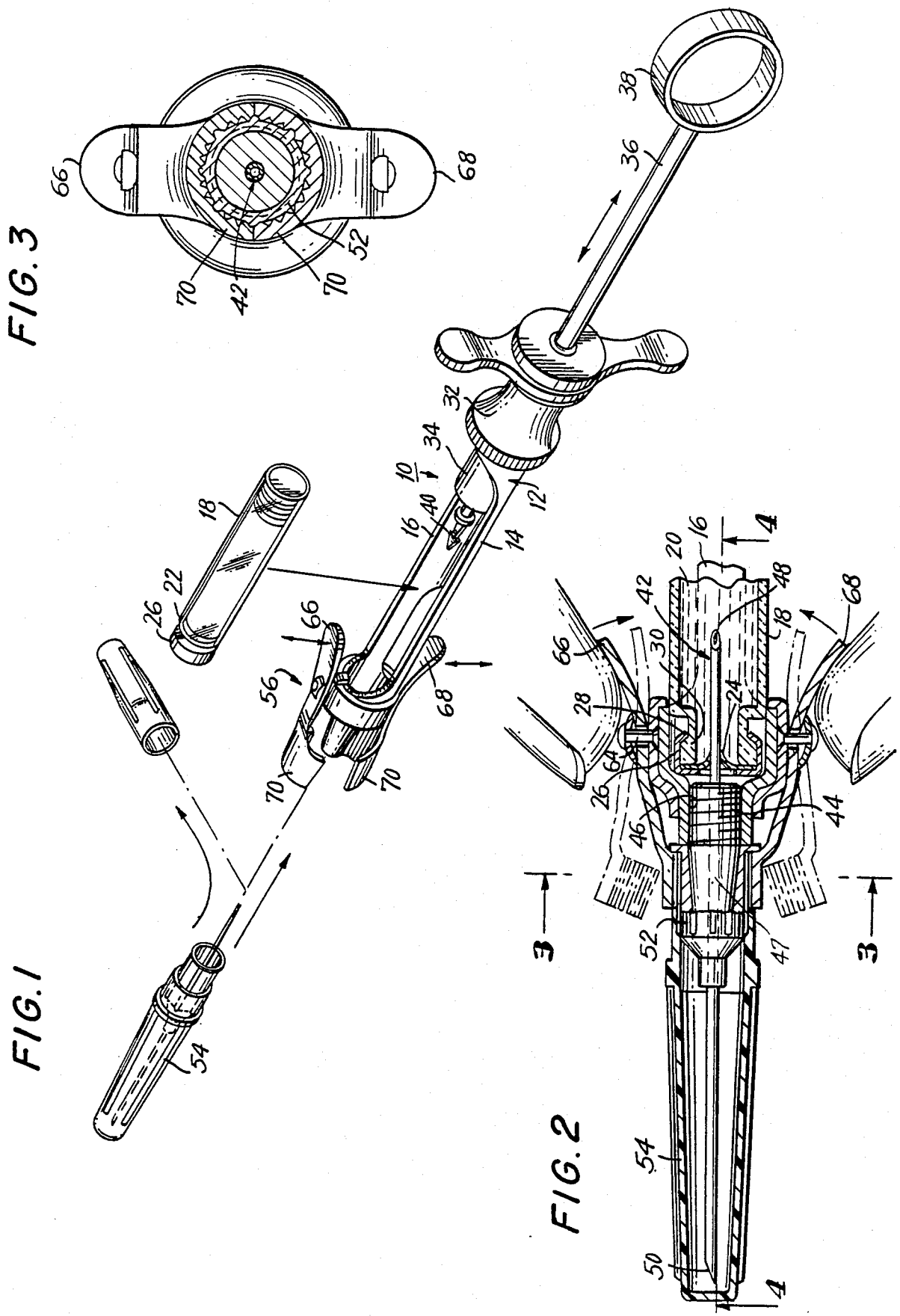

CARPULE SYRINGE WITH RAPIDLY ACTING MECHANISM FOR CONTROLLABLY POSITIVELY RETAINING THE HUB OF A HYPODERMIC NEEDLE

RELATED APPLICATION

This application is a continuation in part of patent application, Ser. No. 380,605, filed May 21, 1982 for Carpule Syringe Rention Means now abandoned.

BACKGROUND OF THE INVENTION

1. Field of the Invention

Carpule syringe with equipment for detachably and positively holding the hub of a hypodermic needle.

2. Description of the Prior Art

Carpule syringes are a relatively new entry into the medical field. They have come to be widely used and accepted, particularly where syringes are to be loaded and used repetitively. Syringes of this nature facilitate repeated loading. They lend themselves well to rapid, simple and easy insertion of fresh doses of medicament and discharge of exhausted containers. A carpule syringe, also known as a cartridge syringe, is characterized by the absence, as in a standard syringe, of a fixed barrel in which a piston reciprocates. Instead, a carpule syringe includes a frame with a large side opening designed to transversely receive a pre-filled, i.e. loaded, cartridge, the ends of which are closed and hermetically sealed. After insertion in the frame, the cartridge is locked in place. The forward end of the cartridge is closed by a plug that includes a thin, easily penetratable, self-sealing membrane. The rear end of the cartridge is closed by a plug which is capable of slidable movement within the cartridge. The frame is provided with a reciprocatable shaft arranged to be engaged with the plug under the control of an operator so that when the shaft is pushed forwardly in the frame, it will push the plug forwardly and thereby apply pressure to the liquid medicament within the cartridge so as to dispense the same through a hypodermic needle. A special hypodermic needle is used which is located at the front of the frame. This needle has a hub between its ends which is screwed into the front of the frame. The needle includes a rearwardly extended pointed segment which pierces the thin membrane at the front of the cartridge when the cartridge is inserted in the frame so as to couple the needle to the liquid medicament. Such arrangement enables cartridge after cartridge to be inserted into the frame where it is immediately ready for use, to be used until exhausted and to be replaced with a fresh cartridge time after time, quickly and expeditiously.

Carpules, of course, like all other medical equipment, have their problems. A major problem is that the connection between the hub of the syringe and the front of the frame is a threaded one. The hub has a male thread and the frame has a female thread. One of these threads wears out after extended use, usually the thread on the frame. It seems a matter of fate that when the failure occurs it is at an inopportune time, namely, when the syringe is embedded in a patient's flesh. When this occurs, after injection, and the doctor or clinician tries to pull out the needle, all that he will succeed in doing is to pull the frame away, leaving the needle with the attached hub embedded in the patient's flesh. The needle now must be delicately removed from the patient, usually with considerable discomfort and anxiety to the patient. This happens with far too great frequency. It is the purpose of the present invention to avoid this particular difficulty.

One proposal has been made to solve the problem above mentioned. This is embodied in Lingley U.S. Pat. No. 2,806,473 in which a carpule type syringe uses a double-ended syringe needle the inner end of which is disposed to pierce the seal at the outer end of the cartridge and in which a clip on the frame presses a hub of the needle against the frame of the syringe. The problem is not the same as the problem with which applicant is concerned, inasmuch as applicant's problem is unique to a carpule type syringe in which the needle has a hub screwed into the frame of the syringe, so that the needle is used repeatedly and there is an erosion of the joint between the hub and the syringe frame, i.e. of the mechanical coupling between the hub and the frame. The same distinction is true of Macgregor U.S. Pat. No. 2,695,613. Kauffman U.S. Pat. No. 2,047,512 and Burnside U.S. Pat. No. 2,604,890 represent other approaches to the same problem which are not relevent because they are not designed to function with commercially available carpule syringes having a female threaded front end. Haines U.S. Pat. No. 1,591,761 discloses a hypodermic syringe which employs a clamp to lock in place a needle hub the frusto conical socket of which is seated on a frusto conical tip at the discharge end of the syringe barrel; however the syringe is not a carpule type syringe.

SUMMARY OF THE INVENTION

1. Purposes of the Invention

It is an object of this invention to provide a carpule syringe including a positive, rapid acting, secure needle hub retention means constituting relatively few and simple parts which is comparatively inexpensive to make and is highly reliable in operation.

It is another object of the invention to provide a carpule syringe of the character described which is easy to disassemble for purposes of sterilization and can be employed by unskilled, non-medical personnel without extensive instructions.

It is another object of the invention to provide a carpule syringe of the character described which lends itself to mass production.

It is a further object of the invention to provide a carpule syringe of the character described which avoids the pain and suffering attendant upon the use of present-day syringes of previous constructions.

Other objects of the invention in part will be obvious and in part will be pointed out hereinafter.

2. Brief Description of the Invention

In keeping with these objects and others which will become apparent hereinafter, one feature of this invention resides, briefly stated, in a carpule syringe which has been modified to include a clamp that is spring biased to a closed position around the hub of a carpule hypodermic needle directly below the carpule frame, and which is mounted on the frame whereby to lock the hub in its operative position onto the frame so that it will not tend to shift in a direction axially of the frame and thereby be able to experience movement relative to the frame in an axial direction when the frame is pulled away from a patient in whom the hypodermic needle of the syringe is at the moment embedded. Such clamp is conveniently provided with manually operable handles, the tips of which are spaced from the body of the carpule frame whereby any pressure thereon toward the frame will release the operative portions of the clamp and, hence, permit the carpule needle to be removed from the carpule under the control of the operator. Biasing means is included to bias the clamp to closed position so that the operation of the clamp is away from its normally closed position. The hub of the needle has a frusto conical seat which is received on a frusto conical plug mounted into the female thread at the discharge end of the carpule syringe.

The invention consists in the features of construction, combination of elements, arrangement of parts and series of steps which will be exemplified in the device hereinafter described and of which the scope of application will be indicated in the appended claims.

BRIEF DESCRIPTION OF THE DRAWINGS

Referring now in detail to the drawings:

FIG. 1 is an exploded perspective view of a carpule syringe constructed in accordance with and embodying the present invention;

FIG. 2 is an enlarged axial sectional view of the front end of the syringe taken through the clamp, the clamp being shown in closed position in solid lines and in open position in dot-and-dash lines;

FIGS. 3 and 4 are sectional views taken substantially along the lines 3—3 and 4—4, respectively, of FIG. 2;

DETAILED DESCRIPTION OF THE PREFERRED EMBODIMENT

Figure 5:
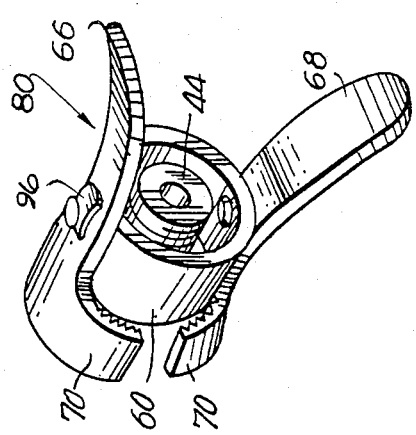
FIG. 5 is a view similar to FIG. 2 of a modified form of the invention.

Referring now in detail to the drawings, and more particularly to FIGS. 1-4, the reference numeral 10 denotes a conventional carpule syringe of substantially standard construction which will now be described in detail as background for the instant invention. This description is purely exemplificative as that of a standard carpule syringe. It will be appreciated that the carpule syringe may vary in construction without departing from the spirit of the invention which resides in the clamp hereinafter detailed which is used to hold the syringe needle to the syringe frame. It is in this clamp that the invention resides. However, the functioning of the clamp cannot be understood or appreciated without a previous description of all of the elements of a conventional carpule syringe.

Thus, the carpule syringe includes a frame 12 of rigid material such, for example, as metal. The frame is composed of several pieces, one of which constitutes a tube 14, the side of which is deeply cut away to form a transverse opening 16 that is large enough to admit a carpule 18 introduced from the side of the syringe. When introduced, the carpule is full of a liquid medicament 20 as clearly shown in FIGS. 2, 4 and 6. The end of the carpule which is to be located at the front end of the frame and which is referenced with the numeral 22, i.e. the front end of the carpule, is closed by a thin membrane 24. Conventionally, this is an elastomeric membrane, e.g. a rubber membrane, which is easily penetratable and preferably self-sealing. Moreover, this front end of the carpule has the membrane held in place and additionally sealed by a thin metal cap 26, the periphery 28 of which is spun back over a bead 30 integral with the front end 22 of the carpule, thereby locking the membrane in place.

The rear end of the carpule is sealed by a rubber piston (not shown). Typically, such a rubber piston is illustrated and referenced 65 in U.S. Pat. No. 3,848,593 to Baldwin, dated Nov. 19, 1974, which here is mentioned by way of example as illustrative of a typical carpule with front and back closures such as are being described herein with respect to the carpule 18.

The rubber piston is capable of sliding movement within and longitudinally of the carpule 18 and, upon longitudinal movement toward the front end 22 of the carpule, will create pressure on the liquid medicament sufficient to eject it from the carpule when provided with a proper exit as hereinafter will be described.

Figure 4:
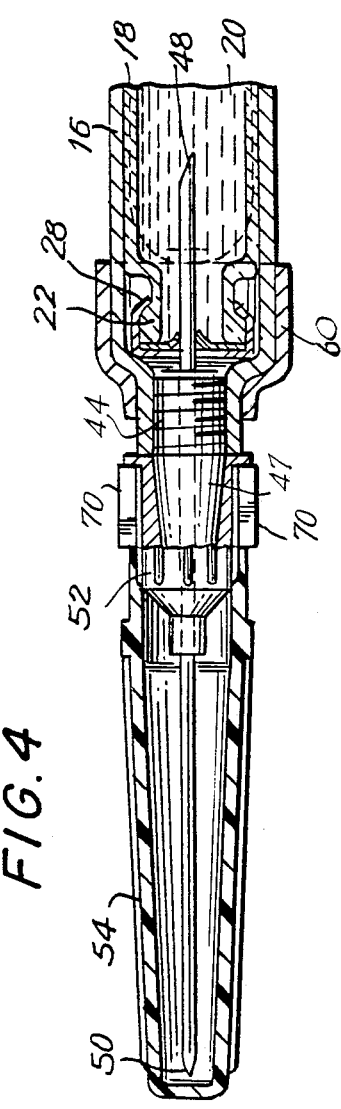
Figure 6:
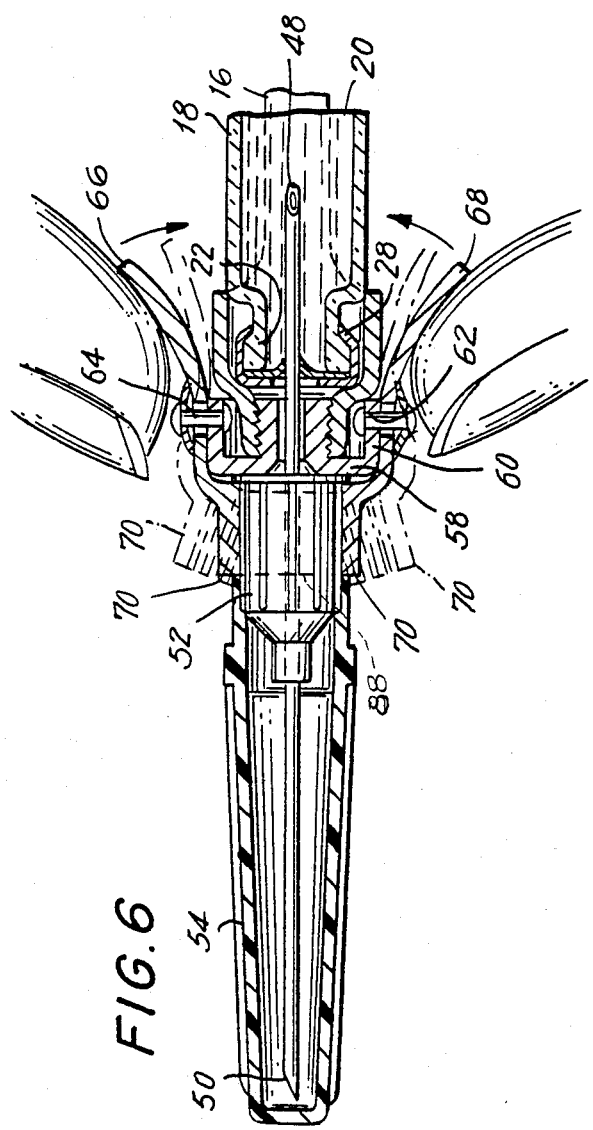
FIG. 6 is a perspective view of the clamp employed in the form of the invention shown in FIG. 5.

The front end of the frame is complete so as to fully receive the front end of the carpule as best is shown in FIGS. 2, 4 and 6; that is to say, at the front end of the frame the front end of the carpule is fully received within the frame.

The rear end of the tube 14, as originally formed, is open and is provided with a male thread (not shown) to threadedly receive a knurled metal cap 32. A metal sleeve 34 has its rear end slidably accommodated within the metal cap and its forward end extending into the tube 14. This sleeve is biased forwardly by a spring (not shown). The sleeve is pushed back when it is desired to insert a carpule into the frame, and then the sleeve slides forwardly to resiliently hold a carpule between the front end of the sleeve and the front end of the frame, thereby to secure the carpule in the frame. At this time the carpule is, in effect, locked in the frame.

A piston rod 36 is reciprocatable under manual control in the sleeve 34, the rod being engageable by a finger with the aid of a handle 38. The forward end of the piston rod is supplied with a barb 40. When a carpule is in place within the tube, held there by the resilient pressure of the spring, and the piston rod is pressed forwardly, the barb will engage the center of the rubber piston (not shown) and become embedded therein. Thereafter, when the rod is pressed further, it will force the rubber piston downwardly into the carpule so as to eject liquid medicament through a suitable exit (not yet described). Thereafter, if the piston rod is moved rearwardly, it engages the rubber piston, retracts the piston and pulls the same toward the rear of the frame.

To provide a suitable exit for the liquid medicament, a double-ended hypodermic needle 42 is provided. A male threaded tubular plug 44 is screwed into a female threaded bore 46 which is conventionally provided at the discharge end of a standard carpule type syringe 10. This bore 46 heretofore has received a male threaded hub of a double-ended hypodermic needle. However, this arrangement is not employed in accordance with the present invention. It is a threaded connection between a male threaded hub of a double-ended hypodermic needle and the female threaded discharge end of a carpule syringe which has tended to deteriorate over long periods of use, this being the problem which is remedied by the instant invention. The plug 44 has a tubular extension 47 which is forwardly tapering. The degree of taper is quite slight, typically being about 3°, and is so small that it hardly can be seen in the drawings. An attempt has been made to illustrate a small degree of taper, but the taper is so tiny that it may not be noticeable at first blush and, indeed, may be lost in reproduction. The portion of the hypodermic needle extending rearwardly of the needle hub has a sharpened point 48, and the portion of the hypodermic needle extending forwardly of the needle hub has a sharpened point 50.

The sharpened point is used in the normal manner for subdermal injections. The sharpened point 48 is employed, as is conventional, for piercing the membrane 24 after passing through the hollow centers of the extension 47 and plug 44. This point 48 easily penetrates the membrane when the hub is coupled to the tip 47, at such time as a carpule is in place on the frame. The hub is denoted by the reference numeral 52. It is provided with a tapered internal socket, the angle of which substantially matches the angle of the tip 47 so that the two make a good fit when they are mated. The hub may be longitudinally ribbed to facilitate its handling during a coupling maneuver.

It will be observed that by providing the plug 44, which is screwed into the female bore 46 and left permanently in place, a forward tapered tip 47 is provided for the carpule syringe to which a double-ended needle can be detachably coupled time after time without ever downgrading the efficiency of the communiction between the hub and the carpule as heretofore has been the case where the double-ended needle had a male threaded hub which was repeatedly screwed into and unscrewed from the female threaded bore and the discharge end of the carpule. It will, of course, be appreciated that this repeated coupling and uncoupling of this double-ended needle to the carpule frame, is necessary, because after a carpule has been exhausted or replaced the carpule cannot be removed and a fresh carpule inserted until the sharpened point 48 first is removed from the membrane 24 before a similar membrane of a fresh carpule is provided. In order to protect the forwardly projecting portion of the needle and the sharpened point 50 it is usual to provide a sheath, typically of plastic, which engages the hub 52.

Through the the foregoing construction which has substituted a tapered male/female joint for a threaded male/female joint for connection of the double-ended needle hub to the discharge end of the carpule, a major advantage and object of the present invention has been attained. Further, pursuant to the present invention, and in order to stabilize and lock the needle in place and, thereby, positively prevent the needle from becoming disconnected from the syringe while the syringe is being used so as to prevent the possibility of, when an operator tries to remove the needle from a patient, that the needle might be left imbedded in a patient's flesh while the syringe is pulled away requiring manual manipulation of the needle hub, suitable means is included to the foregoing end. Such means constitutes a clamp which is a necessary element of the instant invention. The clamp provides an arrangement for readily, quickly, easily and positively connecting the hub to the frame. More specifically, the clamp, which is indicated by the general reference numeral 56, is permanently mounted so as to form part of the frame 14 as by the use of a ring 60 which tightly embraces the forward end of the frame. The forward end of the ring is spun onto the reduced front end of the syringe frame as can be seen quite clearly in FIG. 2 and a pair of tabs 58 at the rear edge of the ring are bent inwardly to overlie the rim of the cutaway edge of the front portion of the frame whereby the clamp is firmly and permanently locked in place so it can serve as a secure foundation for the clamp 56. The ring 60 is formed with a pair of diametrically opposed radially extending openings 62 that receive pins 64, the heads of which lie within the ring.

Clamp arms 66, 68 line on the outside of the ring 60 in a diametrically opposed relationship being pierced by slots to pass the pins 64. The outer heads of the pins compress spring washers, i.e. Belleville washers, against the outer surfaces of the clamps thereby spreading the undersurfaces of the rims of the clamps so that the centers of the Belleville washers are forced up against the heads of the pins. This, in turn, forces the jaws 70 of the clamps inwardly toward each other. The jaws engage the outer surface at the front of the hub 52 so as to maintain it and the association double-ended needle of the hub in their proper positions. It will do this even, as usually will not be the case, if the tapered engagement between the tip 47 and the socket of the hub should slightly loosen. It will be observed that the rear end of the hub 52 has an outwardly extending annular flange and that the rear ends of the jaws 70 lie immediately in front of the front surface of the flange to inhibit any tendency of this flange to move forwardly, so that not only is the hub protected against radial movement, but also against axial movement. Obviously, the hub cannot move axially rearwardly because of the forward taper of the tip 47 and the matching taper of the socket in the hub.

To release the hub and, hence, the double pointed needle from the frame, one simply needs to urge the rear ends of the jaws towards each other as shown in dot and dash lines in FIG. 2. This will urge the front ends apart and will permit the hub 52 to be pulled off the tip 47 and the point 48 to be pulled out of the membrane 24. Hence, the clamp 56 fully controls the engagement of the hub of the hypodermic syringe to the frame and it is a very simple manipulation to engage the hub to or disengage the hub from the frame.

In FIGS. 5 and 6 there is shown a slightly modified form of the invention. The modification resides in the mode of connection of the clamp to the carpule syringe frame. It will be recalled that in the form of the invention shown in FIGS. 1 through 4 the clamp was mounted on a frame with the assistance of a ring 60 permanently secured to the front end of the syringe 14 that a forwardly tapering tip 47 was provided with the aid of a plug that was screwed into the female thread conventionally supplied at the discharge end of a carpule frame. This arrangement has been altered in this form of the invention. Here, wherein the parts of the carpule syringe are identical to those shown in FIGS. 1 through 4 and bear the same reference numerals, a clamp bearing the general reference numeral 80 has been provided. This clamp is supported by a male threaded plug 44 which screws into a female bore 46 at the front of the frame 14 and is intended to be permantly emplaced in such position. The forward end of the plug 44 has a pair of diametrically outwardly extending supporting legs 58 supporting a ring 60 similar to the ring 60 in the first described form of the invention.

Supported on the forward end of the plug 44 is a forwardly tapering tip 88 similar to the tip 47. Said tip can only be seen by its outline that is shown in dotted lines, since it is concealed in FIG. 5 by a hub 52 of a double-ended hypodermic needle, the inner pointed end 48 of which pierces the membrane 24 and the outer pointed end 50 of which was designed to be used in a normal manner for subdermal injections. The interior of the hub is shaped to provide a rearwardly tapered socket that matches the tapered tip 88 so that when the socket is coupled thereto the two mate nicely. However, this cannot be relied upon, and, as in the case of the needle described with reference to the FIG. 1 through 4 form of the invention, there is provided a clamp 80 to stabilize the hub 52 and its needle. The clamp provides a pair of diametrically opposed jaws 66, 68 pivotally connected to the ring 60 as by pins 64 extending through openings 62 located in diametrically opposed positions in the ring 60. The jaws are shown in their closed position in FIG. 6 in solid lines and in open position in the same figure by dot and dash lines. Belleville washers 96 urge the jaws to closed position, these being arranged in the same manner as described with respect to FIGS. 1 through 4.

In FIG. 6 there is shown the clamp 80 and its mounting means detached from the frame of the carpule syringe but ready to be permanently mounted thereto by screw engagement.

A plastic sheath 54 functionally engages the hub to protect the outer end 50 of the needle. It will be appreciated that the needle is attached to and detached from a carpule frame and, specifically, from the tip 88 in the same fashion as described at some length with respect to the first detailed form of the invention and the same is true of the operation of the clamp 80.

Thus, it will be seen that there are provided devices which accomplish the various objects of the invention and which are adapted to meet the conditions of practical use.

As various possible embodiments need to be made of the above invention and as different variations might be made in the embodiments above set forth, it is to be understood that all material herein described or shown in the accompanying drawings is to be interpreted as illustrative and not in a limiting sense.

Having thus described the invention, there is claimed as new and desired to be secured by Letters Patent:

1. A carpule syringe having a frame with a forward end provided with a female threaded bore, a tubular plug with a male thread screwed into the female threaded bore of the syringe frame, said plug having a forwardly tapered tubular extension designed to receive and frictionally engage the tapered socket of a double-ended hypodermic needle, said needle including a hub with a tapered socket dimensioned to matingly frictionally engage the tapered extension of the plug, said hub supporting a rearwardly extending sharpened point adapted to pierce a diaphragm of a carpule received in the syringe frame and a forwardly extending sharpened point designed to be used for injection of a carpule-contained medicament into a patient, and means to prevent accidental detachment of the needle hub from the tapered extension, said means constituting a pair of clamping arms having jaws, means to pivotally mount said clamping arms at diametrically opposed positions on the carpule frame, said clamping arms being manually manipulatable to urge their jaws apart and spring means to bias the jaws together against opposite sides of the hub.

2. A carpule syringe as set forth in claim 1 in which the springs means constitutes a Belleville washer disposed between each clamping arm and the mounting means therefor.

3. A carpule syringe as set forth in claim 1 wherein the pivotal mounting means constitutes a ring and wherein the spring means constitutes a different Belleville spring washer for each of the different clamping arms.

4. A carpule syringe as set forth in claim 1 wherein the pivotal mounting means constitutes a ring circumferentially surrounding the lower end of the syringe frame and having unitary portions at its upper and lower edges which overlie portions of the carpule frame so as to lock the ring in place.

5. A carpule syringe as set forth in claim 1 wherein the pivotal mounting means constitutes a ring in one piece with the plug.

6. A carpule syringe having a frame with a forward end provided with a forwardly tapered tubular tip designed to receive and frictionally engage the tapered socket of the hub of a double-ended hypodermic needle, said hub supporting a rearwardly extending sharpened point adapted to pierce a diaphragm of a carpule received in the syringe frame and a forwardly extending sharpened point designed to be used for injection of a carpule-contained medicament into a patient, and means to prevent accidental detachment of the needle hub from the tapered tip, said means constituting a pair of clamping arms having jaws, means to pibotally mount said clamping arms at diametrically opposed positions on the carpule frame, said clamping arms being manually manipulatable to urge their jaws apart and spring means to bias the jaws against opposite sides of the hub.

* * * * *